(12) United States Patent
De La Poterie et al.

(10) Patent No.: US 7,998,465 B2
(45) Date of Patent: Aug. 16, 2011

(54) HEAT-SWELLING COSMETIC COMPOSITION

(75) Inventors: Valérie De La Poterie, Lailly-En-Val (FR); Thérèse Daubige, Beaumont En Veron (FR)

(73) Assignee: L'Oreal S.A., Paris (FR)

( * ) Notice: Subject to any disclaimer, the term of this patent is extended or adjusted under 35 U.S.C. 154(b) by 1551 days.

(21) Appl. No.: 10/969,019

(22) Filed: Oct. 21, 2004

(65) Prior Publication Data

US 2005/0175648 A1 Aug. 11, 2005

Related U.S. Application Data

(60) Provisional application No. 60/516,760, filed on Nov. 4, 2003.

(30) Foreign Application Priority Data

Oct. 24, 2003 (FR) .................................... 03 12503

(51) Int. Cl.
*A61Q 1/10* (2006.01)
*A61Q 1/06* (2006.01)

(52) U.S. Cl. .......................... 424/70.7; 424/64; 424/401

(58) Field of Classification Search .................. None
See application file for complete search history.

(56) References Cited

U.S. PATENT DOCUMENTS

| | | | |
|---|---|---|---|
| 3,615,972 A | 10/1971 | Morehouse, Jr. | |
| 4,964,429 A | 10/1990 | Cole | |
| 5,593,680 A * | 1/1997 | Bara et al. | 424/401 |
| 5,853,010 A * | 12/1998 | Suh | 132/217 |
| 5,853,910 A | 12/1998 | Tomioka et al. | |
| 5,914,117 A | 6/1999 | Lavaud | |
| 6,009,884 A | 1/2000 | Suh | |
| 6,045,783 A | 4/2000 | Macchio et al. | |
| 2001/0055580 A1 | 12/2001 | Belli et al. | |
| 2004/0126345 A1 | 7/2004 | McNamara | |

FOREIGN PATENT DOCUMENTS

| | | |
|---|---|---|
| EP | 0 056 219 A1 | 7/1982 |
| EP | 0 112 807 A2 | 7/1984 |
| EP | 0 320 473 A1 | 6/1989 |
| EP | 0 348 372 | 12/1989 |
| EP | 0 486 080 A2 | 5/1992 |
| EP | 1 228 747 A2 | 8/2002 |
| FR | 2700952 * | 8/1994 |
| WO | WO 03/028679 A1 | 4/2003 |

* cited by examiner

*Primary Examiner* — Jyothsna Venkat
(74) *Attorney, Agent, or Firm* — Finnegan, Henderson, Farabow, Garrett & Dunner LLP

(57) ABSTRACT

Disclosed herein is a cosmetic composition comprising at least one heat-expandable compound. Further disclosed herein a cosmetic treatment process, comprising applying to a support to be treated the composition and a packaging and application assembly.

28 Claims, 1 Drawing Sheet

HEAT-SWELLING COSMETIC COMPOSITION

This non-provisional application claims the benefit of French Application No. 03 12503 filed on Oct. 24, 2003 and U.S. Provisional Application No. 60/516,760 filed on Nov. 4, 2003.

The present disclosure relates to cosmetic compositions comprising at least one heat-expandable compound, i.e., a compound capable of swelling on heating, wherein these compositions are capable of giving volume when they are subjected to a source of heat.

The term "giving volume", also referred to below as "volumizing effect," is an effect that is frequently sought in the cosmetics field.

For example, in the field of eyelash makeup, very concentrated mascara formulations with a high solids content, making it possible to deposit a large thickness of material, have been proposed. However, such formulations may have the drawback of having a very thick consistency and thus being difficult to apply. Also in the field of mascaras, conversely, very fluid formulations have been proposed, which, by superposition of coats, also make it possible to obtain a volumizing effect. However, in this case, the conditions for obtaining the volumizing effect are not entirely satisfactory either since they may be time-consuming and difficult to implement.

For the lips, the volumizing effect has hitherto been obtained either by drawing a lip contour that is larger than the natural contour, or by employing optical effects, for example, using glossy compositions.

Another alternative includes using, in cosmetic compositions, polymers with a high capacity for water absorption. When applied to its makeup site, the composition is placed in contact with water leading to an increase in its initial volume, thus generating the desired volumizing effect. Such compositions are described, for example, in U.S. Pat. No. 6,045,783 and document EP 1 228 747. However, the compositions with a volumizing effect using these polymers may be unsatisfactory since, in order to obtain significant swelling, a relatively large amount of water needs to be supplied. Furthermore, this swelling may not be long-lasting and may be reversible on evaporation of the water.

It has now been discovered by the present inventors that it is possible to obtain cosmetic compositions capable of generating an advantageous volumizing effect, where the volumizing effect can last for a sustained period of time.

Accordingly, the present disclosure relates to a cosmetic composition, in particular a heat-expandable cosmetic composition, comprising at least one heat-expandable compound, i.e., a compound capable of swelling on heating.

The term "heat-expandable composition," as used herein, means a composition capable of expanding, i.e. a composition capable of increasing its volume, on heating. As used herein, "swelling" and "expanding" are interchangeable.

In addition, the present disclosure relates to a cosmetic composition comprising at least one heat-expandable particle.

The present disclosure also relates to a cosmetic treatment process comprising applying the composition as defined above to a support to be treated.

Further disclosed herein is a made-up support comprising a makeup that may be obtained according to the process as defined above.

Another aspect of the present disclosure is an assembly for packaging and applying a makeup and/or care composition, such as for the eyelashes or the eyebrows, as defined above, comprising:
  i) a reservoir comprising the composition,
  ii) a device for applying the composition; and
  iii) a heating device.

The present disclosure also relates to the use of heat-expandable particles as defined above as additives for giving a volumizing effect to a cosmetic composition under the effect of heat.

As emerges from the examples below, the compositions as disclosed herein can show a significant volumizing effect. For example, the initial volume of the composition, i.e., the volume obtained after applying the composition to the support to be treated, may be increased, in response to a source of heat, by a multiplication factor of at least 1.5, such as 2, further such as 2.5 and 3 and even further such as up to 10. This volumizing effect may, for example, be proportional to the content of the compound capable of swelling on heating.

This volumizing effect may be assessed by measuring the thickness of the composition applied to the support to be treated, before heating and after heating. In the case of an eyelash makeup composition, this effect may be characterized by measuring the diameter of the made-up fiber.

This volumizing effect can be obtained within a few seconds and can be long-lasting.

Compound Capable of Swelling on Heating

As indicated above, the compositions disclosed herein comprise at least one compound capable of swelling on heating.

It may, for example, be a compound that reacts, under the action of heat, to release a gas that is trapped within the matrix of the deposit.

The compound capable of swelling on heating may also be in the form of heat-expandable particles.

The term "heat-expandable particles," as used herein, means particles capable of becoming deformed and of expanding on heating. The particles as disclosed herein may also be non-expanded heat-deformable particles. They are distinguished in this respect from expanded particles, which are, specifically, no longer subject to deformation under the action of heat in a manner, for example, of the polyvinylidene chloride/acrylonitrile particles sold under the generic name Expancel® by the company Akzo Nobel, under the references of, for example, Expancel® WE and DE.

The particles used in the compositions as disclosed herein are capable of expanding under the action of a temperature generally of greater than or equal to 45° C., such as greater than or equal to 50° C., further such as greater than or equal to 60° C., and even further such as greater than or equal to 70° C. For example, it may be a temperature of greater than or equal to 80° C., such as greater than or equal to 85° C., further such as greater than or equal to 90° C., and even further such as greater than or equal to 100° C. In one embodiment, the temperature ranges from 190° C. to 200° C.

Advantageously, these particles are not sensitive to the presence of water.

In addition, the deformation and expansion of the particles under the effect of heat are irreversible.

In one embodiment, the particles used herein are thermoplastic. The term "thermoplastic," as used herein, means particles that are capable of becoming deformed under the action of heat and capable of keeping their new shape, including after cooling, for example, to room temperature (25° C.).

The particles used herein are, for example, generally hollow particles comprising a continuous envelope and at least one cavity.

The envelope of the particles is flexible to allow mechanical deformation. It generally comprises, for example, at least one polymer chosen from homopolymers and copolymers, formed from ethylenically unsaturated monomers. Examples of such particles are described, for instance, in documents EP-A-56219, EP-A-348 372, EP-A486 080, EP-A-320 473, and EP-A-112 807 and U.S. Pat. No. 3,615,972.

The monomers used may, for example, be chosen from methacrylic and acrylic acid esters, such as methyl acrylate and methacrylate, vinylidene chloride, acrylonitrile, styrene and derivatives thereof, butadiene and derivatives thereof, and mixtures thereof.

As non-limiting illustrations of the polymers of which the envelope of the particles used in the present disclosure may be composed, mention may be made, for example, of polymers comprising at least one monomeric unit chosen from methyl acrylate and methyl methacrylate derivatives, polymers comprising at least one monomeric unit chosen from acrylonitrile derivatives, polymers comprising at least one monomeric unit chosen from acrylonitrile and methyl methacrylate derivatives, polymers comprising at least one monomeric unit chosen from styrene and acrylonitrile derivatives, polymers comprising at least one monomeric unit chosen from vinylidene chloride and acrylonitrile derivatives, and polymers comprising at least one monomeric unit chosen from vinylidene chloride and vinyl chloride derivatives. For example, the polymer may be chosen from vinylidene chloride/acrylonitrile/methyl methacrylate polymers, acrylonitrile/methyl methacrylate polymers and acrylonitrile homopolymers.

The particles generally, for example, comprise, within the at least one cavity, at least one compound capable of exhibiting, in response to heating to a temperature ranging from 45° C. to 200° C. and at substantially constant pressure, a significant increase in its volume relative to its volume at room temperature.

The term "significant increase in its volume," as used herein, means an increase by at least a factor of 30, such as by at least a factor of 40 and further such as by at least a factor of 50 of its volume relative to the occupied volume prior to the heating.

In general, the at least one compound within the cavity may be chosen from, at room temperature, gaseous compounds and liquid compounds with a vaporization temperature ranging from 45° C. to 200° C., such as from 80° C. to 200° C. and further such as from 100° C. to 200° C.

In one embodiment, the at least one compound within the cavity of the particles is in the gaseous form in the particle and becomes dilated under the effect of heat. Among the compounds in gaseous form at room temperature and atmospheric pressure ($10^5$ Pa), mention may be, for example, made of air, nitrogen, hydrocarbons such as those comprising from 1 to 4 carbon atoms, for instance butane and isobutane, and mixtures thereof.

In another embodiment, the at least one compound within the cavity of the particles is a liquid compound at room temperature and atmospheric pressure ($10^5$ Pa). Among these compounds, mention may be made, for example, of hydrocarbons, comprising from 5 to 15, such as from 5 to 12 and further such as from 5 to 10 carbon atoms. It may be, for example, a compound chosen from n-pentane, isopentane and neopentane.

The expansion temperature of the particle depends both on the nature of the compound present in its cavity and the nature of the polymer forming its envelope, and may range, for example, from 45 to 200° C., and may, for example, be greater than or equal to 70° C., such as greater than or equal to 80° C., and further such as greater than or equal to 100° C.

The particles used in the compositions as disclosed herein may be dry or hydrated.

These particles may have various shapes. They may be of globular or even spherical shape, or may also be elongated.

In one embodiment, the non-expanded heat deformable particles as disclosed herein are spherical and have a particle size, expressed as the weight-average "effective" diameter D[0,5], ranging from 0.5 µm to 200 µm, such as from 1 µm to 100 µm, further such as from 4 µm to 50 µm, and even further such as from 5 µm to 40 µm.

In another embodiment, the particles used in the compositions as disclosed herein have a fiber form. The term "fiber," as used herein, means an object of length L and of diameter D such that L is very much greater than D, wherein D is the diameter of the circle within which the cross section of the fiber is inscribed. For example, the ratio L/D (or form factor) ranges from 3.5:1 to 2500:1, such as from 5:1 to 500:1, and further such as from 5:1 to 150:1. The fibers may, for example, have a length ranging from 0.05 mm to 6 mm.

The non-expanded heat deformable particles used herein generally have a mass per unit volume ranging, for example, from 500 kg/m$^3$ to 5000 kg/m$^3$, such as from 900 kg/m$^3$ to 3000 kg/m$^3$ and further such as from 900 kg/m$^3$ to 2000 kg/m$^3$.

The particles used herein may be colored or colorless.

As particles that may be used in the compositions as disclosed herein, examples that may be mentioned include non-expanded microspheres of vinylidene chloride/acrylonitrile/methyl methacrylate copolymer, for instance those sold under the name Expancel® by the company Akzo Nobel under the references 820 DU 40 (10-16 µm), 820 SL 40 (2-30 µm) and 642 WU (10-16 µm), and non-expanded microspheres of acrylonitrile/methyl methacrylate, for instance those sold under the name Expancel® under the reference 051 DU 40 (9-15 µm). As particles that may also be used in the compositions as disclosed herein, mention may also be made, for example, of non-expanded microspheres of acrylonitrile homopolymer, for instance those sold under the name Expancel 007 WUF 40® (5-25 µm), Micropearl F-series® by the company Matsumoto and Ucelite® by the company UCB.

As particles that may be used in the composition as disclosed herein, mention may also be made, for example, of non-expanded microspheres of polyacrylonitrile treated on their surface with titanium dioxide (TiO$_2$), having a mean diameter of 50 µm, comprising in their cavity a mixture of butane and methane, for example, those sold under the reference MFL 50 STI by the company MATSUMOTO.

The particles sold under the name Expancel® as disclosed above generally comprise in their cavity a compound in gaseous form.

Needless to say, the particles used in the composition as disclosed herein are chosen according to the desired type of composition and the heating device to be used.

The heat-expandable particles as defined above are generally present in the compositions as disclosed herein in an amount ranging, for example, from 0.05% to 50%, such as from 0.1% to 40% and further such as from 0.5% to 30% by weight relative to the total weight of the composition.

Cosmetically Acceptable Medium

The compositions as disclosed herein may also comprise at least one cosmetically acceptable medium.

The term "cosmetically acceptable medium," as used herein, means a medium that is compatible with application to the skin, the lips, the nails and keratin fibers.

This medium may be of aqueous or non-aqueous type or may comprise an aqueous phase and a non-aqueous phase, and may be non-volatile or may comprise at least one volatile compound.

When the medium is of aqueous type, it may consist solely of water or may comprise a mixture of water with at least one organic solvent, wherein the at least one organic solvent is generally, for example, water-soluble.

Among these solvents, mention may be made, for example, of lower monoalcohols comprising from 1 to 5 carbon atoms, such as ethanol and isopropanol, glycols comprising from 2 to 8 carbon atoms, such as glycerol, propylene glycol, ethylene glycol, 1,3-butylene glycol and dipropylene glycol, $C_3$-$C_4$ ketones and $C_2$-$C_4$ aldehydes.

When the medium is of non-aqueous type, it comprises less than 20% by weight of water and/or water-soluble solvent, and comprises at least one water-insoluble organic solvent such as oils.

As used herein, the term "volatile medium or compound" means any medium or compound that can evaporate on contact with the skin, the lips, the nails or keratin fibers in less than one hour at room temperature and atmospheric pressure. The volatile medium or compound is liquid at room temperature, such as having a non-zero vapor pressure at room temperature and atmospheric pressure, for example, having a vapor pressure ranging from 0.13 Pa to 40 000 Pa ($10^{-3}$ to 300 mmHg), such as from 1.3 Pa to 13 000 Pa (0.01 to 100 mmHg) and further such as from 1.3 Pa to 1 300 Pa (0.01 to 10 mmHg).

Conversely, the term "non-volatile medium or compound," as used herein, means a medium or compound that remains on the skin, the lips, the nails or keratin fibers at room temperature and atmospheric pressure for more than one hour and that has, for example, a vapor pressure of less than $10^{-3}$ mmHg (0.13 Pa).

The volatile oils that may be mentioned include, for example, hydrocarbon-based oils, silicone oils and fluoro oils, and mixtures thereof.

The term "hydrocarbon-based oil," as used herein, means an oil mainly comprising hydrogen and carbon atoms and possibly at least one atom chosen from oxygen, nitrogen, sulfur and phosphorus atoms. The volatile hydrocarbon-based oils may be chosen, for example, from hydrocarbon-based oils comprising from 8 to 16 carbon atoms, such as branched $C_8$-$C_{16}$ alkanes, for instance $C_8$-$C_{16}$ isoalkanes of petroleum origin (also known as isoparaffins), such as isododecane (also known as 2,2,4,4,6-pentamethylheptane), isodecane, isohexadecane, and for example the oils sold under the trade names Isopars® and Permetyls®, branched $C_8$-$C_{16}$ esters such as isohexyl neopentanoate, and mixtures thereof. Other volatile hydrocarbon-based oils, for instance petroleum distillates, such as those sold under the name Shell Solt® by the company Shell, may also be used.

Volatile oils that may also be used include, for example, volatile silicones, for instance volatile linear or cyclic silicone oils, such as those with a viscosity $\leq 6$ centistokes ($6 \times 10^{-6}$ m$^2$/s) and comprising, for example, from 2 to 10 silicon atoms, these silicones optionally comprising at least one group chosen from alkyl and alkoxy groups comprising from 1 to 22 carbon atoms. As volatile silicone oils that may be used herein, mention may be made, for example, of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Volatile organic compounds that may also be mentioned include, for example, fluorinated organic solvents such as nonafluoromethoxybutane and perfluoromethylcyclopentane.

The medium used in the compositions as disclosed herein may also comprise at least one water-insoluble non-volatile compound that is liquid at room temperature, such as at least one non-volatile oil, which may be chosen, for example, from non-volatile hydrocarbon-based oils, silicone oils, and fluoro oils.

Non-volatile hydrocarbon-based oils that may be mentioned include, for example:

hydrocarbon-based oils of plant origin, such as triglycerides comprising fatty acid esters of glycerol, the fatty acids of which may have varied chain lengths chosen from $C_4$ to $C_{24}$, wherein these chains may be linear or branched, saturated or unsaturated; these oils are chosen, for example, from wheatgerm oil, sunflower oil, grapeseed oil, sesame seed oil, maize oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppyseed oil, pumpkin oil, sesame seed oil, marrow oil, rapeseed oil, blackcurrant oil, evening primrose oil, millet oil, barley oil, quinoa oil, rye oil, safflower oil, candlenut oil, passionflower oil and musk rose oil; and caprylic/capric acid triglycerides, for instance those sold by the company Stéarineries Dubois and those sold under the names Miglyol 810®, 812® and 818® by the company Dynamit Nobel, synthetic ethers comprising from 10 to 40 carbon atoms, linear or branched hydrocarbons of mineral or synthetic origin, such as petroleum jelly, polydecenes, hydrogenated polyisobutene such as parleam, and squalane, and mixtures thereof, synthetic esters, for instance oils of formula $R_1COOR_2$ wherein $R_1$ is chosen from linear and branched fatty acid units comprising from 1 to 40 carbon atoms and $R_2$ is a hydrocarbon-based chain, which may, for example, be branched, comprising from 1 to 40 carbon atoms, on condition that the carbon atoms of ($R_1$+$R_2$)$\geq$10, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, alcohol and polyalcohol heptanoates, octanoates, decanoates and ricinoleates, for instance propylene glycol dioctanoate; hydroxylated esters, for instance isostearyl lactate and diisostearyl malate; and pentaerythritol esters, fatty alcohols that are liquid at room temperature with a branched and/or unsaturated carbon-based chain comprising from 12 to 26 carbon atoms, for instance octyidodecanol, isostearyl alcohol, oleyl alcohol, 2-hexyldecanol, 2-butyloctanol and 2-undecylpentadecanol, and higher fatty acids such as oleic acid, linoleic acid and linolenic acid, and mixtures thereof.

The non-volatile silicone oils that may be used in the composition as disclosed herein may, for example, be chosen from non-volatile polydimethylsiloxanes (PDMS), polydimethylsiloxanes comprising at least one group chosen from alkyl and alkoxy groups, which is pendent and/or at the end of a silicone chain, wherein the at least one group comprises from 2 to 24 carbon atoms, phenylsilicones, for instance phenyl trimethicones, phenyl dimethicones, phenyltrimethylsiloxydiphenylsiloxanes, diphenyl dimethicones, diphenylmethyidiphenyltrisiloxanes and 2-phenylethyltrimethylsiloxysilicates.

The fluoro oils that may be used in the composition as disclosed herein may be chosen, for example, from fluorosilicone oils, fluoro polyethers and fluoro silicones as described in document EP-A-847 752.

The particles are, for example, generally present in dispersion in the cosmetically acceptable medium.

The composition as disclosed herein may also comprise at least one additional cosmetically acceptable ingredient.

The at least one additional cosmetically acceptable ingredient may be chosen, for example, from film-forming polymers, dyestuffs, fillers, thickeners and gelling agents, surfactants, waxes, plasticizers, antioxidants, preserving agents, fragrances, neutralizers and cosmetic active agents, for instance emollients, moisturizers, vitamins and sunscreens, and mixtures thereof.

Thus, in one embodiment, the cosmetic composition further comprises at least one dyestuff.

In another embodiment, the composition as disclosed herein is a makeup cosmetic composition.

In yet another embodiment, the composition as disclosed herein is a makeup cosmetic composition for the keratin fibers.

Film-Forming Polymer

The composition as disclosed herein may thus further comprise at least one film-forming polymer.

As used herein, the term "film-forming polymer" means a polymer capable of forming, by itself or in the presence of an auxiliary film-forming agent, a continuous film that adheres to a support, such as keratin materials.

Among the film-forming polymers that may be used in the composition as disclosed herein, mention may be made, for example, of synthetic polymers, free-radical type and polycondensate type, polymers of natural origin and mixtures thereof.

The film-forming polymers of free-radical type may, for example, be chosen from vinyl polymers and copolymers, such as acrylic polymers.

The vinyl film-forming polymers may result from the polymerization of at least one of ethylenically unsaturated monomers comprising at least one acid group, esters of these acidic monomers, and amides of these acidic monomers, for instance α,β-ethylenic unsaturated carboxylic acids such as acrylic acid, methacrylic acid, crotonic acid, maleic acid and itaconic acid.

The vinyl film-forming polymers may also result from the homopolymerization or copolymerization of monomers chosen from vinyl esters, for instance vinyl acetate, vinyl neodecanoate, vinyl pivalate, vinyl benzoate and vinyl t-butylbenzoate, and styrene monomers, for instance styrene and α-methylstyrene.

The film-forming polycondensates that may be mentioned include, for example, polyurethanes, polyesters, polyesteramides, polyamides and polyureas.

The optionally modified polymers of natural origin may be chosen, for example, from shellac resin, sandarac gum, dammar resins, elemi gums, copal resins and cellulose-based polymers, and mixtures thereof.

The film-forming polymer may be present in the form of particles in aqueous dispersion, generally known as latices or pseudolatices. The techniques for preparing these dispersions are well known to those skilled in the art.

Aqueous dispersions of the film-forming polymer that may be used include, for example, the acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® by the company Daito Kasey Kogyo; and the aqueous dispersions of polyurethane sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, Impranil 85® by the company Bayer, Aquamere H-1511® by the company Hydromer; the sulfopolyesters sold under the brand name Eastman AQ® by the company Eastman Chemical Products, vinylic dispersions, for instance Mexomère PAM and also acrylic dispersions in isododecane, for instance Mexomère PAP by the company Chimex.

When the composition as disclosed herein comprises at least one film-forming polymer, this polymer is generally present in a solids content (or active material content) ranging, for example, from 1% to 40%, such as from 2% to 35% and further such as from 3% to 30% by weight relative to the total weight of the composition.

The composition as disclosed herein may also comprise at least one auxiliary film-forming agent that promotes the formation of a film with the film-forming polymer.

Dyestuff

The composition as disclosed herein may also comprise at least one dyestuff, chosen, for example, from pulverulent dyes, liposoluble dyes and water-soluble dyes.

The pulverulent dyestuffs may be chosen from pigments and nacres.

The pigments may be white or colored, mineral and/or organic, and coated or uncoated. The mineral pigments that may be mentioned include, for example, titanium dioxide, optionally surface-treated, zirconium oxide, zinc oxide, cerium oxide, iron oxide, chromium oxide, manganese violet, ultramarine blue, chromium hydrate and ferric blue. The organic pigments that may be mentioned include, for example, carbon black, pigments of D & C type, and lakes based on cochineal carmine or on barium, strontium, calcium or aluminium.

The nacres may be chosen from white nacreous pigments such as mica coated with titanium or with bismuth oxychloride, colored nacreous pigments such as titanium mica with iron oxides, titanium mica with, for example, ferric blue and chromium oxide, titanium mica with an organic pigment of the abovementioned type, and also nacreous pigments based on bismuth oxychloride.

The liposoluble dyes are chosen, for example, from Sudan Red, D&C Red 17, D&C Green 6, β-carotene, soybean oil, Sudan Brown, D&C Yellow 11, D&C Violet 2, D&C Orange 5, quinoline yellow and annatto.

These dyestuffs may be present in an amount ranging, for example, from 0.01% to 30% by weight relative to the total weight of the composition.

Fillers

The composition as disclosed herein may also comprise at least one filler.

The fillers may be chosen from those that are well known to persons skilled in the art and commonly used in cosmetic compositions. The fillers may be mineral or organic, and lamellar or spherical. Mention may be made, for example, of talc, mica, silica, kaolin, polyamide powders, for instance the Nylon® sold under the trade name Orgasol® by the company Atochem, poly-β-alanine powders and polyethylene powders, powders of tetrafluoroethylene polymers, for instance Teflon®, lauroyllysine, starch, boron nitride, expanded polymeric hollow microspheres such as those of polyvinylidene chloride/-acrylonitrile, for instance the products sold under the name Expancel® by the company under the references DE and WE Nobel Azko, acrylic powders, such as those sold under the name Polytrap® by the company Dow Corning, polymethyl methacrylate particles and silicone resin microbeads (for example Tospearls® from Toshiba), precipitated calcium carbonate, magnesium carbonate and magnesium hydrocarbonate, hydroxyapatite, hollow silica microspheres (Silica Beads® from Maprecos), glass or ceramic microcapsules, metal soaps derived from organic carboxylic acids comprising from 8 to 22 carbon atoms such as from 12 to 18 carbon atoms, for example zinc, magnesium and lithium stearates, zinc laurate and magnesium myristate.

The at least one filler may be present in an amount ranging, for example, from 0.1% to 25%, such as from 1% to 20%, by weight relative to the total weight of the composition.

Gelling Agent

Gelling agents that may be used in the compositions as disclosed herein may be organic or mineral, polymeric or molecular, and lipophilic or hydrophilic.

Mineral lipophilic gelling agents that may be mentioned include, for example, optionally modified clays, for instance hectorites modified with a $C_{10}$ to $C_{22}$ fatty acid ammonium chloride, for instance hectorite modified with distearyldimethylammonium chloride, such as the product sold under the name Bentone 38V® by the company Elementis.

Mention may also be made of fumed silica optionally subjected to a hydrophobic surface treatment, the particle size of which is less than 1 μm. Specifically, it is possible to chemically modify the surface of the silica, by chemical reaction generating a reduced number of silanol groups present at the surface of the silica. It is, for example, possible to substitute silanol groups with hydrophobic groups: a hydrophobic silica is then obtained. The hydrophobic groups may be chosen, for example, from:

trimethylsiloxyl groups, which are obtained, for example, by treating fumed silica in the presence of hexamethyidisilazane. Silicas thus treated are known as "silica silylate" according to the CTFA (6th edition, 1995). They are sold, for example, under the references Aerosil R812® by the company Degussa, and Cab-O-Sil TS-530® by the company Cabot; and dimethylsilyloxyl and polydimethylsiloxane groups, which are obtained, for example, by treating fumed silica in the presence of polydimethylsiloxane or dimethyldichlorosilane. Silicas thus treated are known as "silica dimethyl silylate" according to the CTFA (6th edition, 1995). They are sold, for example, under the references Aerosil R972® and Aerosil R974® by the company Degussa, and Cab-O-Sil TS-610® and Cab-O-Sil TS-720® by the company Cabot.

The hydrophobic fumed silica has, for example, a particle size that may be nanometric to micrometric, for example, ranging from 5 to 200 nm.

The polymeric organic lipophilic gelling agents are, for example, partially or totally crosslinked elastomeric organopolysiloxanes of three-dimensional structure, for instance those sold under the names KSG6®, KSG16® and KSG18® from Shin-Etsu, Trefil E-505C® and Trefil E-506C® from Dow Corning, Gransil SR-CYC®, SR DMF 10®, SR-DC556®, SR 5CYC gel®, SR DMF 10 gel® and SR DC 556 gel® from Grant Industries and SF 1204® and JK 113® from General Electric; ethylcelluloses, for instance the product sold under the name Ethocel by Dow Chemical and galactomannans comprising from one to six such as from two to four hydroxyl groups per saccharide, substituted with at least one chain chosen from saturated and unsaturated alkyl chains, for instance guar gum alkylated with at least one alkyl chain chosen from $C_1$ to $C_6$, such as $C_1$ to $C_3$, alkyl chains, and mixtures thereof. Block copolymers of "diblock" or "triblock" type, of the polystyrene/polyisoprene or polystyrene/polybutadiene type such as the products sold under the name Luvitol HSB® by the company BASF, block copolymers of the polystyrene/copoly(ethylene-propylene) type such as the products sold under the name Kraton® by the company Shell Chemical Co., and block copolymers of the polystyrene/copoly(ethylene-butylene) type may also be used.

Among the gelling agents that may be used in the compositions as disclosed herein, mention may also be made, for example, of fatty acid esters of dextrin, such as dextrin palmitates, for example, the products sold under the names Rheopearl TL® and Rheopearl KL® by the company Chiba Flour.

The gelling agents may be present in an amount ranging, for example, from 0.1% to 15%, such as from 0.5% to 10%, by weight relative to the total weight of the composition.

Surfactants:

The composition as disclosed herein may also comprise at least one surfactant present in an amount ranging, for example, from 0.1% to 30% by weight, such as from 2% to 20% by weight and further such as from 5% to 15% by weight relative to the total weight of the composition.

The at least one surfactant may be chosen, for example, from anionic and nonionic surfactants. Reference may be made to the document "Encyclopedia of Chemical Technology, Kirk-Othmer", volume 22, pp. 333-432, 3rd edition, 1979, Wiley, for the definition of the properties and functions (emulsifying) of surfactants, in particular pp. 347-377 of this reference, for the anionic and nonionic surfactants.

The surfactants used in the composition as disclosed herein are chosen, for example, from:

among the nonionic surfactants: fatty acids, fatty alcohols, polyethoxylated and polyglycerolated fatty alcohols such as polyethoxylated stearyl and cetylstearyl alcohol, fatty acid esters of sucrose, alkylglucose esters, such as polyoxyethylenated $C_1$-$C_6$ alkylglucose fatty esters, and mixtures thereof, and among the anionic surfactants: $C_{16}$-$C_{30}$ fatty acids neutralized with at least one of amines, aqueous ammonia and alkaline salts, and mixtures thereof.

Wax(es)

The composition as disclosed herein may also comprise at least one wax.

The term "wax," as used herein, generally means a lipophilic compound that is solid at room temperature (25° C.), with a solid/liquid reversible change of state, having a melting point of greater than or equal to 30° C., which may be up to 200° C. In one embodiment, the at least one wax has a melting point of 120° C.

By bringing the wax to the liquid form (melting), it is possible to make it miscible with oils and to form a microscopically uniform mixture, but on cooling the mixture to room temperature, recrystallization of the wax in the oils of the mixture is obtained.

For example, the waxes that are suitable for use herein may have a melting point of greater than or equal to 45° C. such as greater than or equal to 55° C.

As used herein, the melting point corresponds to the temperature of the most endothermic peak observed by thermal analysis (DSC) as described in ISO standard 11357-3 (1999). The melting point of the wax may be measured using a differential scanning calorimeter (DSC), for example, the calorimeter sold under the name MDSC 2920 by the company TA Instruments.

The measuring protocol is as follows:

A sample of 5 mg of wax placed in a crucible is subjected to a first temperature rise ranging from −20° C. to 100° C., at a heating rate of 10° C./minute, it is then cooled from 100° C. to −20° C. at a cooling rate of 10° C./minute and is finally subjected to a second temperature increase ranging from −20° C. to 100° C. at a heating rate of 5° C./minute. During the second temperature increase, the variation of the difference in power absorbed by the empty crucible and by the crucible containing the sample of wax is measured as a function of the temperature. The melting point of the compound is the temperature value corresponding to the top of the peak of the curve representing the variation in the difference in absorbed power as a function of the temperature.

The waxes that may be used in the compositions as disclosed herein are chosen, for example, from waxes that are solid at room temperature of animal, plant, mineral and synthetic origins, and mixtures thereof.

The waxes that may be used in the compositions as disclosed herein generally have a hardness ranging, for example, from 0.01 MPa to 15 MPa, such as greater than 0.05 MPa and further such as greater than 0.1 MPa.

The hardness is determined by measuring the compression force, measured at 20° C. using a texturometer sold under the name TA-XT2i® by the company Rheo, equipped with a stainless-steel cylindrical spindle 2 mm in diameter, by measuring the change in force (compression force or stretching force) (F) as a function of time, during the following operation:

The spindle is displaced at a speed of 0.1 mm/s and then penetrates the wax to a penetration depth of 0.3 mm. When the spindle has penetrated the wax to a depth of 0.3 mm, the spindle is held still for 1 second (corresponding to the relaxation time) and is then withdrawn at a speed of 0.1 mm/s. During the relaxation time, the force (compression force) decreases greatly until it becomes zero, and then, during the withdrawal of the spindle, the force (stretching force) becomes negative and then rises again towards the value 0. The hardness corresponds to the maximum compression force measured between the surface of the spindle and the wax at the moment they come into contact. The value of this force is expressed in MPa.

To measure the hardness, the wax is melted at a temperature equal to the melting point of the wax +20° C. The molten wax is poured into a container 30 mm in diameter and 20 mm deep. The wax is recrystallized at room temperature (25° C.) for 24 hours and is then stored for at least 1 hour at 20° C., before the hardness measurement is performed.

As illustrations of waxes that are suitable herein, mention may be made, for example, of hydrocarbon-based waxes, for instance beeswax, lanolin wax, Chinese insect waxes, rice wax, carnauba wax, candelilla wax, ouricurry wax, esparto grass wax, cork fibre wax, sugar cane wax, Japan wax and sumach wax; montan wax, microcrystalline waxes, paraffins and ozokerite; polyethylene waxes, the waxes obtained by Fischer-Tropsch synthesis and waxy copolymers, and also esters thereof.

Mention may also be made, for example, of waxes obtained by catalytic hydrogenation of animal or plant oils comprising at least one chain chosen from linear and branched $C_8$-$C_{32}$ fatty chains. These waxes that may be mentioned include, for example, isomerized jojoba oil such as the trans-isomerized partially hydrogenated jojoba oil manufactured or sold by the company Desert Whale under the reference Iso-Jojoba-50®, hydrogenated sunflower oil, hydrogenated castor oil, hydrogenated coconut oil, hydrogenated lanolin oil and bis(1,1,1-trimethylolpropane) tetrastearate sold under the name Hest 2T-4S® by the company Heterene.

Mention may also be made, for example, of silicone waxes and fluoro waxes.

The waxes obtained by hydrogenation of castor oil esterified with cetyl alcohol, sold under the names Phytowax ricin 16L64® and 22L73® by the company Sophim may also be used. Such waxes are described in patent application FR-A-2 792 190.

In one embodiment, the compositions as disclosed herein may comprise at least one "tacky" wax, i.e. a wax with a tack of greater than or equal to 0.7 N.s and a hardness of less than or equal to 3.5 MPa.

The tacky wax used may, for example, have a tack ranging from 0.7 N.s to 30 N.s, such as greater than or equal to 1 N.s, further such as from 1 N.s to 20 N.s, for example, greater than or equal to 2 N.s, and further such as from 2 N.s to 10 N.s, for example, from 2 N.s to 5 N.s.

The tack of the wax is determined by measuring the change in force (compression force or stretching force) as a function of time, at 20° C., using the texturometer sold under the name TA-TX2i® by the company Rheo, equipped with a conical acrylic polymer spindle forming an angle of 45°.

The measuring protocol is as follows:

The wax is melted at a temperature equal to the melting point of the wax+10° C. The molten wax is poured into a container 25 mm in diameter and 20 mm deep. The wax is recrystallized at room temperature (25° C.) for 24 hours such that the surface of the wax is flat and smooth, and the wax is then stored for at least 1 hour at 20° C. before measuring the tack.

The texturometer spindle is displaced at a speed of 0.5 mm/s then penetrates the wax to a penetration depth of 2 mm. When the spindle has penetrated the wax to a depth of 2 mm, the spindle is held still for 1 second (corresponding to the relaxation time) and is then withdrawn at a speed of 0.5 mm/s.

During the relaxation time, the force (compression force) decreases greatly until it becomes zero, and then, during the withdrawal of the spindle, the force (stretching force) becomes negative and then rises again to the value 0. The tack corresponds to the integral of the curve of the force as a function of time for the part of the curve corresponding to negative values of the force (stretching force). The tack value is expressed in N.s.

The tacky wax that may be used generally, for example, has a hardness of less than or equal to 3.5 MPa, such as ranging from 0.01 MPa to 3.5 MPa, further such as from 0.05 MPa to 3 MPa and even further such as from 0.1 MPa to 2.5 MPa.

The hardness is measured according to the protocol described previously.

The tacky waxes that may be used include, for example, a $C_{20}$-$C_{40}$ alkyl (hydroxystearyloxy)stearate (wherein the alkyl group comprises from 20 to 40 carbon atoms), alone or as a mixture, such as a $C_{20}$-$C_{40}$ alkyl 12-(12'-hydroxystearyloxy)stearate, of formula (I):

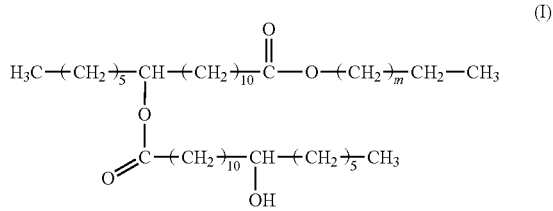

wherein m is an integer ranging from 18 to 38, or a mixture of compounds of formula (I).

Such a wax is, for example, sold under the names Kester Wax K 82 P® and Kester Wax K 80 P® by the company Koster Keunen.

The waxes mentioned above generally have, for example, a starting melting point of less than 45° C.

The at least one wax may be in the form of an aqueous microdispersion of wax particles. The term "aqueous microdispersion of wax" means an aqueous dispersion of wax particles in which the size of the wax particles is less than or equal to 1 µm.

Wax microdispersions are stable dispersions of colloidal wax particles, and are described, for example, in "Microemulsions Theory and Practice", L. M. Prince Ed., Academic Press (1977) pages 21-32.

For example, these wax microdispersions may be obtained by melting the wax in the presence of at least one surfactant, and optionally of a portion of water, followed by gradual addition of hot water with stirring. The intermediate formation of an emulsion of the water-in-oil type is observed, followed by a phase inversion, with final production of a microemulsion of the oil-in-water type. On cooling, a stable microdispersion of solid wax colloidal particles is obtained.

The wax microdispersions may also be obtained by stirring the mixture of wax, surfactant and water using stirring implement such as ultrasound, high-pressure homogenizers and turbomixers.

The particles of the wax microdispersion have, for example, a mean particle size of less than 1 µm (such as ranging from 0.02 µm to 0.99 µm) and, for example, less than or equal to 0.5 µm (such as ranging from 0.06 µm to 0.5 µm).

These particles consist essentially of a wax or a mixture of waxes. However, they may comprise a small proportion of at least one ingredient chosen from oily and pasty fatty additives, surfactants and common liposoluble additive/active agents.

Needless to say, at least one of these waxes or a mixture may be used in the composition as disclosed herein.

When the composition as disclosed herein comprises at least one wax, the at least one wax is generally present in an amount ranging, for example, from 1% to 60% by weight, such as from 2% to 50% and further such as from 3% to 40% by weight relative to the total weight of the composition.

Depending on the nature of the medium and the optional additional ingredients used, the composition as disclosed herein may be of aqueous, aqueous-alcoholic, non-aqueous or even anhydrous type, or alternatively may be in the form of a W/O or O/W emulsion.

Needless to say, the choice of the type of composition, the medium and the additional ingredients depends on the intended purpose of the composition. For example, the composition as disclosed herein may be a makeup composition such as a mascara, an eyeliner, a lipstick or a composition for drawing an inscription of tattoo type on the nails, the skin or the hair. It may also be a cosmetic care composition for filling in the wrinkles and fine lines of the skin of the lips in order to obtain a smoothing effect. It may also be a haircare composition for producing a volumizing effect on the hair or on certain areas thereof, or alternatively decorative relief effects through its swelling power.

The compositions as described above are generally capable of swelling on heating at a temperature of greater than or equal to 45° C., such as greater than or equal to 50° C., further such as greater than or equal to 60° C., and even further such as greater than or equal to 70° C.

As indicated previously, the present disclosure also relates to a cosmetic treatment process, such as a makeup process using the composition as defined above. This process comprises applying the composition to the support to be treated. It also generally comprises heating the composition, such as during or after its application.

The heating of the composition is performed under conditions that allow an increase in the volume of the composition relative to the volume it occupies prior to being heated.

The support to be treated may be the skin, the lips, the nails and keratin fibers. The term "keratin fibers," as used herein, means any fiber consisting essentially of keratin, such as head hair, other bodily hairs, the eyelashes and the eyebrows.

The support to be treated may also be a makeup accessory, for instance false eyelashes, wigs or pastilles or patches that adhere to the skin or the lips (such as beauty spots).

In the process as disclosed herein, the composition is, for example, generally heated to a temperature of greater than or equal to 45° C., such as greater than or equal to 50° C., further such as greater than or equal to 60° C. and even further such as greater than or equal to 70° C. The heating temperature depends, for example, on the temperature that may be tolerated by the treated support.

In one embodiment, the composition is heated during its application. In such a case, the heating implement used is, for example, generally the applicator itself. Thus, in the case of a mascara, the composition may be applied using a heating brush.

In another embodiment, the composition is heated after it has been applied. According to a first variant, the composition may be heated using a device not specifically intended for heating, for instance a body that is occasionally hot, such as a hot cup and a hot drink. According to a second variant of this embodiment, the composition may be heated using a device specifically dedicated to heating. This may be, for example, a device for propelling hot air such as a hairdryer or a heating device. Non-limiting examples are described below.

The composition as disclosed herein may be packaged in a packaging and application assembly comprising:

i) a reservoir comprising the composition,
ii) a device for applying the composition; and
iii) a heating device.

According to one embodiment, the heating device is a device that is different from the application device or member, wherein the assembly is configured in the form of a packaging and the application device also comprises a container comprising the composition as disclosed herein. Such a device may be packaged in packaging of the blister pack type. The heating device may be of the type described in U.S. Pat. Nos. 6,009,884 and 5,853,010. Other devices configured in the form of a heating brush (in the case of the eyelashes) may also be used. Such devices are described, for example, in U.S. Pat. No. 6,220,252.

DESCRIPTION OF THE DRAWING

The kit 1 described in FIG. 1 comprises a mascara packaging and application assembly 100 and a heating device 50, separate from the packaging and application assembly.

The two devices 100 and 50 may be sold together in the same packaging, of blister-pack type. The packaging and application assembly 100 comprising the composition may be sold separately.

Figure 1:
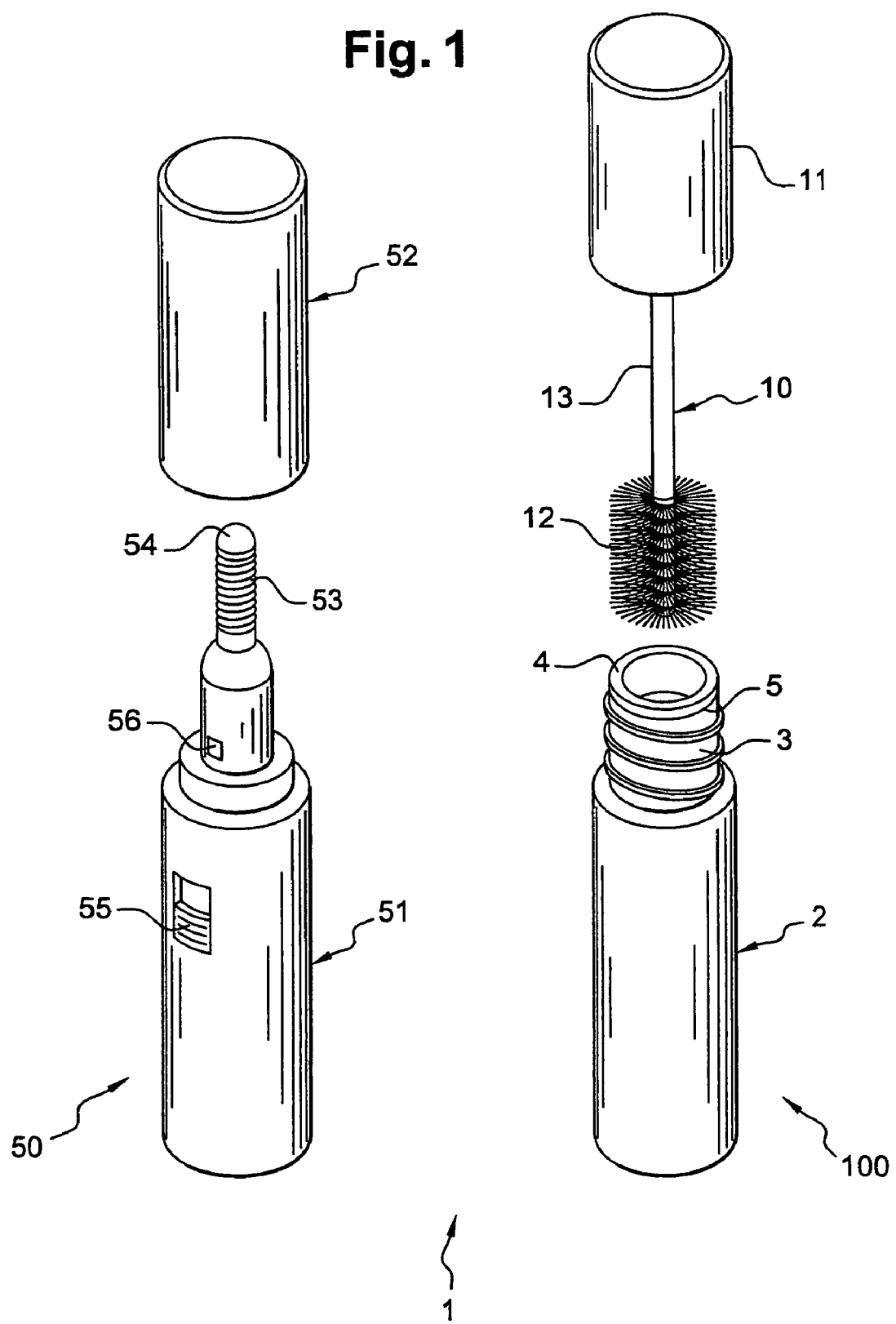

The packaging and application assembly 100 comprises a container 2, comprising the composition as disclosed herein, on which is mounted a threaded collar 3, one free edge of which delimits an opening 4. In the opening 4 is mounted a draining member 5. The assembly 100 also comprises an application device 10 comprising a stopper 11 solidly fastened to a stem 13, one end of which comprises an applicator 12, generally configured in the form of an arrangement of fibers held between the two branches of a twisted iron wire. An inner surface of the stopper 11 is threaded so as to engage with the threading of the neck 3. Thus, when the applicator 12 and the stem 13 are inside the container 2, the threading of the stopper 11 engages with the threading of the neck 3 such that the stopper sealably closes the opening 4 of the container. Such packaging and application assemblies are well known.

The heating device 50 is, for example, in accordance with that described in U.S. Pat. No. 6,009,884. It comprises a grip portion 51 and a lid 52. A battery is placed inside the grip portion 51 and is connected to a heating wire 53 configured in the form of a coil arranged on a stem 54. A "switch" 55 allows the device to be switched on and off. An LED 56, when it changes color, indicates that the device is at the required temperature, and is thus ready for use.

The power supply of the heating part via the battery is 12 V. The power dissipated is about 1 watt. The heating wire 53 may be made of a nickel/chromium alloy.

According to this embodiment, the mascara is applied without heating in a conventional manner to the eyelashes using a brush 12, and is then heated after application: the user engages the heating part 53 of the device 50 on the eyelashes so as to bring the deposit of product to the expansion temperature of the composition.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result. The amounts are given as percentages by weight of the total weight of the composition.

EXAMPLES

In the examples below, the contents are expressed as weight percentages. AM means active material.

Example 1

Mascara Composition

| | |
|---|---|
| Non-expanded heat deformable particles sold under the name Expancel 007 WUF 40 ® by the company Akzo Nobel | 10 |
| Hydroxyethylcellulose | 1.71 |

-continued

| | |
|---|---|
| Talc | 4.5 |
| Propylene glycol | 6.48 |
| Black iron oxide | 4.5 |
| Preserving agent | 0.2 |
| Acrylic latex sold under the name Syntran 5760 ® by the company Interpolymer, at 40% AM | 54 |
| Water | qs 100 |

The in vitro swelling characteristics of this mascara composition were studied.

This study was performed on a sample of false eyelashes (Caucasian hair) on which only three eyelashes were left.

The composition was applied to each of the eyelashes by ten passages. The thickness was measured after drying for 5 minutes at room temperature and then after heating the made-up eyelashes to 100° C. using a hairdryer until swelling of the deposit took place.

Three types of measurement were made for each of the eyelashes: (i) naked eyelash, (ii) made-up eyelash and (iii) made-up and heated eyelash, by means of a "Navitar" camera using the (×2.5) eyepiece. Each measurement was performed in triplicate with calculation of the mean obtained.

The results are given in Table 1 below.

TABLE 1

| | Diameter of the naked eyelash (μm) | Diameter of the made-up eyelash after drying at room temperature (μm) | Diameter of the made-up eyelash heated to 100° C. with a hairdryer (μm) |
|---|---|---|---|
| Eyelash 1 | 92.1 ± 1 | 124 ± 0.8 | 215 ± 6.2 |
| Eyelash 2 | 61.5 ± 0.7 | 111 ± 3 | 240 ± 4 |
| Eyelash 3 | 67.48 ± 0.8 | 108.2 ± 1.7 | 330 ± 27 |

It is noted that the use of the makeup process described above makes it possible to double or even to multiply by a factor of 4.89, in the case of eyelash No 3, the diameter of the eyelash.

It is noted that the use of the heating step alone makes it possible to multiply by a factor of at least 3 the thickness of the mascara composition.

The mascara of Example 1 thus shows a satisfactory volumizing effect.

Example 2

Eyeliner Composition

| | |
|---|---|
| Non-expanded heat deformable particles sold under the name Expancel 820DU 40 ® by the company Akzo Nobel | 5 |
| Acrylic dispersion sold under the name Mexomer PAP ® by the company Chimex, at 24.5% AM | 71.4 |
| Mixture of butylene/ethylene/Styrene triblock copolymer and of ethylene/propylene/Styrene starburst copolymer in isododecane, sold under the name Versagel MD 960 ® by the company Penreco | 1.3 |
| 2-Octyldodecanol | 0.33 |
| Parleam oil | 0.77 |
| Vinylpyrrolidone/1-eicosene copolymer sold under the name Antaron V220 ® by the company ISP | 0.44 |
| Phenyl trimethicone | 0.77 |
| Black iron oxide | 15 |
| Isododecane | qs 100 |

Example 3

Mascara Composition of Emulsion Type

| | |
|---|---|
| Non-expanded heat deformable particles sold under the name Expancel 007 WUF 40 ® by the company Akzo Nobel | 10 |
| $C_{20}$-$C_{40}$ alkyl (hydroxystearoyloxy)stearate wax sold under the name Kester Wax K82 P ® by the company Koster Keunen | 22.5 |
| Candelilla wax | 5.4 |
| Stearic acid | 5.2 |
| Black iron oxide | 5 |
| Aminomethylpropanediol | 0.45 |
| Isononyl isononanoate | 2.7 |
| Hydroxyethylcellulose | 0.82 |
| Gum arabic | 3.1 |
| Triethanolamine | 2.16 |
| Preserving agents | 0.41 |
| Water | qs 100 |

Example 4

Anhydrous Lipstick Composition of Soft Paste Type (Gloss)

| | |
|---|---|
| Poly(diglyceryl 2-acryladipate) | 16.14 |
| Diisostearyl malate | 8.76 |
| Tridecyl trimellilate | 9.31 |
| $C_{18-36}$ acid triglyceride | 17.69 |
| Dimethyl silylate silica | 8 |
| Pigments | 2.05 |
| Nacre | 3 |
| Polybutene | 12 |
| Pentaerythrityl tetraisostearate | 12.42 |
| Non-expanded heat deformable particles sold under the name Expancel 007 WUF 40 ® by the company Akzo Nobel | 10 |
| Fragrance, preserving agents | qs |

This lipstick was prepared by grinding the pigments in some of the oily phase. The rest of the oily phase was heated in a jacketed heating pan on an oil bath (90-95°) with polyisobutene. The ground material was added thereto with continued heating and stirring using a Rayneri stirrer until homogenization was complete. The nacre was then gradually added, followed by addition of the silica with continued stirring and heating at 90-95° C. until a homogeneous mixture was obtained.

After cooling the mixture to room temperature, the Expancel 007 WU® particles were added with stirring using the Rayneri stirrer, until homogeneous dispersion of the particles was obtained.

Although the present disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present invention as defined by the appended claims.

What is claimed is:

1. A cosmetic composition in the form of a mascara comprising at least one heat-expandable compound in the form of heat-expandable particles, wherein said heat-expandable particles are thermoplastic, non-expanded and have a mass per unit volume ranging from 500 kg/m³ to 5000 kg/m³;

wherein said heat-expandable particles are hollow particles comprising a continuous envelope and at least one cavity, wherein said envelope comprises at least one polymer chosen from vinylidene chloride/acrylonitrile/methyl methacrylate copolymers, acrylonitrile/methyl methacrylate copolymers and acrylonitrile homopolymer, and wherein said at least one cavity comprises gas capable of exhibiting, in response to heating to a temperature ranging from 45° C. to 200° C., an increase by at least a factor of 30 of its volume relative to its volume at room temperature, wherein said gas is chosen from air, nitrogen and gaseous hydrocarbons, and mixtures thereof.

2. The cosmetic composition according to claim 1, wherein the composition itself is heat-expandable.

3. The cosmetic composition according to claim 1, wherein the heat-expandable particles are capable of expanding at a temperature of greater than or equal to 45° C.

4. The cosmetic composition according to claim 3, wherein the heat-expandable particles are capable of expanding at a temperature of greater than or equal to 50° C.

5. The cosmetic composition according to claim 4, wherein the heat-expandable particles are capable of expanding at a temperature of greater than or equal to 60° C.

6. The cosmetic composition according to claim 5, wherein the heat-expandable particles are capable of expanding at a temperature of greater than or equal to 70° C.

7. The cosmetic composition according to claim 6, wherein the heat-expandable particles are capable of expanding at a temperature of greater than or equal to 80° C.

8. The cosmetic composition according to claim 7, wherein the heat-expandable particles are capable of expanding at a temperature of greater than or equal to 85° C.

9. The cosmetic composition according to claim 8, wherein the heat-expandable particles are capable of expanding at a temperature of greater than or equal to 90° C.

10. The cosmetic composition according to claim 9, wherein the heat-expandable particles are capable of expanding at a temperature of greater than or equal to 100° C.

11. The cosmetic composition according to claim 1, wherein said heat-expandable particles are globular or elongated.

12. The cosmetic composition according to claim 11, wherein said heat-expandable particles are spherical and have a particle size, expressed as the weight-average effective diameter, ranging from 0.5 µm to 200 µm.

13. The cosmetic composition according to claim 12, wherein the particle size ranges from 1 µm to 100 µm.

14. The cosmetic composition according to claim 13, wherein the particle size ranges from 4 µm to 50 µm.

15. The cosmetic composition according to claim 14, wherein the particle size ranges from 5 µm to 40 µm.

16. The cosmetic composition according to claim 1, wherein said heat-expandable particles have a mass per unit volume ranging from 900 kg/m³ to 3000 kg/m³.

17. The cosmetic composition according to claim 16, wherein said heat-expandable particles have a mass per unit volume ranging from 900 kg/m³ to 2000 kg/m³.

18. The cosmetic composition according to claim 1, wherein said heat-expandable particles are present in an amount ranging from 0.05% to 50% by weight relative to the total weight of the composition.

19. The cosmetic composition according to claim 18, wherein said heat-expandable particles are present in an amount ranging from 0.1% to 40% by weight relative to the total weight of the composition.

20. The cosmetic composition according to claim 19, wherein said heat-expandable particles are present in an amount ranging from 0.5% to 30% by weight relative to the total weight of the composition.

21. The cosmetic composition according to claim 1, further comprising a cosmetically acceptable medium.

22. The cosmetic composition according to claim 1, wherein the composition is capable of swelling on heating at a temperature of greater than or equal to 45° C.

23. The cosmetic composition according to claim 22, wherein the composition is capable of swelling on heating at a temperature of greater than or equal to 50° C.

24. The cosmetic composition according to claim 23, wherein the composition is capable of swelling on heating at a temperature of greater than or equal to 60° C.

25. The cosmetic composition according to claim 24, wherein the composition is capable of swelling on heating at a temperature of greater than or equal to 70° C.

26. The cosmetic composition according to claim 1, further comprising at least one additional cosmetically acceptable ingredient chosen from film-forming polymers, dyestuffs, fillers, thickeners or gelling agents, surfactants, waxes, plasticizers, antioxidants, preserving agents, fragrances, neutralizers and cosmetic active agents.

27. The cosmetic composition according to claim 1, further comprising at least one dyestuff.

28. A method of giving a volumizing effect of a cosmetic composition, in the form of a mascara, under a condition of heating, comprising including in the composition an effective amount of heat-expandable particles,
wherein said heat-expandable particles are thermoplastic, non-expanded and have a mass per unit volume ranging from 500 kg/m$^3$ to 5000 kg/m$^3$;
wherein said heat-expandable particles are hollow particles comprising a continuous envelope and at least one cavity,
wherein said envelope comprises at least one polymer chosen from vinylidene chloride/acrylonitrile/methyl methacrylate copolymers, acrylonitrile/methyl methacrylate copolymers and acrylonitrile homopolymer, and
wherein said at least one cavity comprises qas capable of exhibiting, in response to heating to a temperature ranging from 45° C. to 200° C., an increase by at least a factor of 30 of its volume relative to its volume at room temperature, wherein said gas is chosen from air, nitrogen and gaseous hydrocarbons, and mixtures thereof.

* * * * *

UNITED STATES PATENT AND TRADEMARK OFFICE
CERTIFICATE OF CORRECTION

| | | |
|---|---|---|
| PATENT NO. | : 7,998,465 B2 | Page 1 of 1 |
| APPLICATION NO. | : 10/969019 | |
| DATED | : August 16, 2011 | |
| INVENTOR(S) | : Valérie De La Poterie et al. | |

It is certified that error appears in the above-identified patent and that said Letters Patent is hereby corrected as shown below:

Claim 28, col. 20, line 18, "qas" should read --gas--.

Signed and Sealed this
Tenth Day of January, 2012

David J. Kappos
*Director of the United States Patent and Trademark Office*